(12) United States Patent
Jesseph

(10) Patent No.: US 6,569,176 B2
(45) Date of Patent: May 27, 2003

(54) DEVICE AND METHOD FOR IMPROVED DIAGNOSIS AND TREATMENT OF CANCER

(76) Inventor: Jerry M. Jesseph, 2131 Meadow Bluff Ct., Bloomington, IN (US) 47401

( * ) Notice: Subject to any disclaimer, the term of this patent is extended or adjusted under 35 U.S.C. 154(b) by 0 days.

(21) Appl. No.: 09/766,946

(22) Filed: Jan. 22, 2001

(65) Prior Publication Data

US 2001/0007076 A1 Jul. 5, 2001

Related U.S. Application Data

(62) Division of application No. 09/419,538, filed on Oct. 18, 1999, now Pat. No. 6,254,614.

(51) Int. Cl.$^7$ ............................................. A61B 17/32
(52) U.S. Cl. ........................ 606/167; 600/564; 604/22
(58) Field of Search ................... 606/167, 176, 606/180, 170; 600/562, 564, 567; 604/22

(56) References Cited

U.S. PATENT DOCUMENTS

| | | |
|---|---|---|
| 532,236 A | 1/1895 | Hardesty |
| 667,447 A | 2/1901 | Miller |
| 936,434 A | 10/1909 | Eganhouse |
| 1,222,494 A | 4/1917 | Thomas |
| 3,382,867 A | 5/1968 | Reaves |
| 3,608,540 A | 9/1971 | Sartorius |
| 3,785,369 A | 1/1974 | Tallent |
| 3,786,801 A | 1/1974 | Sartorius |
| 3,828,766 A | 8/1974 | Krasnow |
| 3,913,569 A | 10/1975 | Kanonas |
| 4,029,088 A | 6/1977 | Wu |
| 4,111,192 A | 9/1978 | Wu |
| 4,536,387 A | 8/1985 | Sakamoto et al. |
| 4,869,268 A | 9/1989 | Yoon |
| 4,881,550 A | * 11/1989 | Kothe .......................... 600/565 |
| 5,083,570 A | 1/1992 | Mosby |
| 5,099,830 A | 3/1992 | Kishimoto |
| 5,100,406 A | 3/1992 | Panchula |

(List continued on next page.)

FOREIGN PATENT DOCUMENTS

| | | | |
|---|---|---|---|
| EP | 0279358 | * 2/1988 | .................. 606/565 |
| GB | 2191700 | 12/1987 | |

OTHER PUBLICATIONS

*The Breast Cancer Survival Manual,* John Link, M. D., 1998, pp. 20–21.
*False–Positive Results in Dynamic MR Mammography.* Werner a. Kaiser, MD, MRI Clinics of North America, vol. 2, No. 4, Nov. 1994.
*Interstitial Therman Ablation of Fibroadenomas Using Interactive Ultrasound and MRI,* Mumtaz, Harms, Hronas, Cowan, Hyslop, Klimberg, Westbrook, Arkansas Cancer Research Center, University of Arkansas for Medical Sciences.
*Interstitial Laser Lumpectomy Using MRI Guidance as an Alternative to Conventional Breast Conversation Surgery,* Harms, Mumtaz, Hronas, Cowan, Korourian, Klimberg, Henry–Tillman, Westbrook, Arkansas Cancer Research Center, University of Arkansas for Medical Sciences.
*ABBI System, Advanced Breast Biopsy Instrumentation,* Brochure, Auto Suture Company, 1997.

Primary Examiner—Kevin Shaver
Assistant Examiner—Michael B. Priddy
(74) *Attorney, Agent, or Firm*—Woodard, Emhardt, Naughton, Moriarty & McNett

(57) ABSTRACT

A device, in several configurations, which fixes a breast in distended, stable position using negative pressure, and minimizes or halts lymphatic flow from the breast. The invention allows for improvement in imaging and intervention in diagnosis and treatment of early stage human breast cancer. An image-guided system which allows accurate and bloodless access to breast tissue; guided by MRI or CT; using a unique saw and cautery device; in linear and rotary configurations to remove small or large lesions from the breast.

7 Claims, 11 Drawing Sheets

U.S. PATENT DOCUMENTS

| | | |
|---|---|---|
| 5,111,828 A | 5/1992 | Kornberg et al. |
| 5,197,484 A | 3/1993 | Kornberg et al. |
| 5,246,425 A | 9/1993 | Hunsberger et al. |
| 5,267,572 A * | 12/1993 | Bucalo .................. 600/567 |
| 5,346,497 A * | 9/1994 | Simon et al. ............ 606/107 |
| 5,353,804 A | 10/1994 | Kornberg et al. |
| 5,391,166 A * | 2/1995 | Eggers .................. 606/48 |
| 5,415,620 A | 5/1995 | Chen |
| 5,437,280 A | 8/1995 | Hussman |
| 5,499,989 A | 3/1996 | LaBash |
| 5,520,613 A | 5/1996 | Copelan |
| 5,564,438 A | 10/1996 | Merchant |
| 5,632,717 A | 5/1997 | Yoon |
| 5,678,549 A | 10/1997 | Heywand-Koebrunner et al. |
| 5,702,405 A | 12/1997 | Heywang-Koebrunner |
| 5,706,812 A | 1/1998 | Strenk et al. |
| 5,795,308 A | 8/1998 | Russin |
| 5,807,255 A | 9/1998 | Yokota et al. |
| 5,817,034 A | 10/1998 | Milliman et al. |
| 5,830,219 A | 11/1998 | Bird et al. |
| 5,846,244 A | 12/1998 | Cripe |
| 5,913,863 A | 6/1999 | Fischer et al. |
| 5,971,998 A | 10/1999 | Russell et al. |
| 6,010,466 A | 1/2000 | McGeorge |

\* cited by examiner

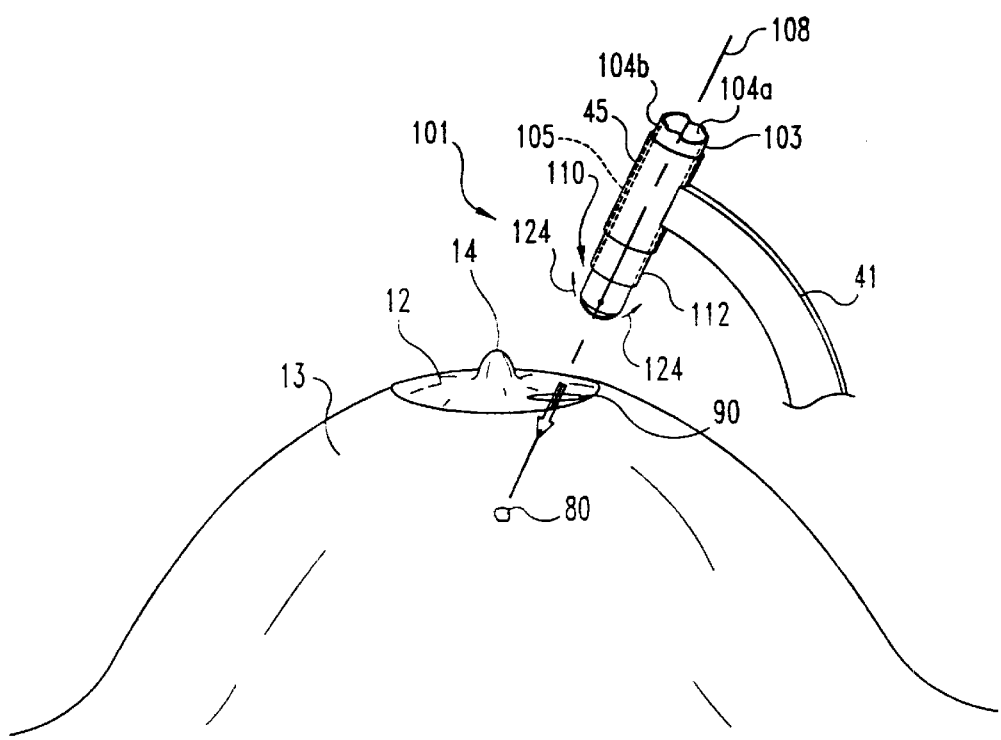
Fig. 5
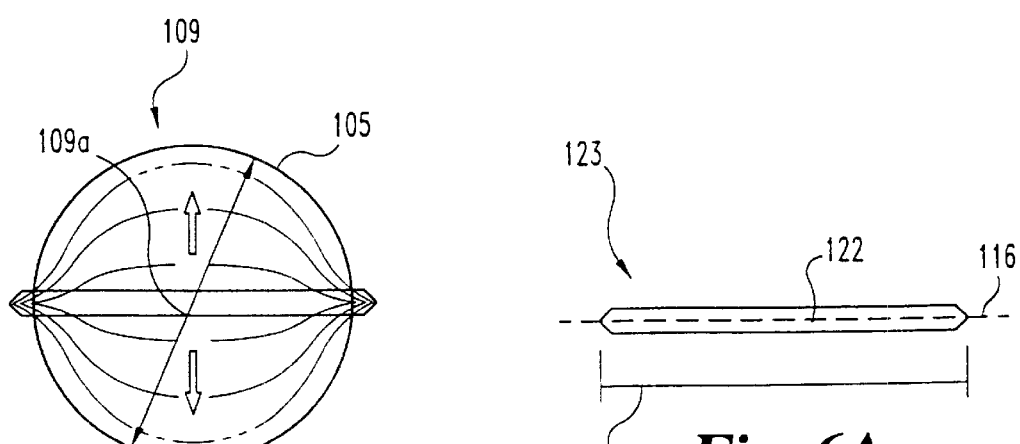
Fig. 6     Fig. 6A

DEVICE AND METHOD FOR IMPROVED DIAGNOSIS AND TREATMENT OF CANCER

CROSS-REFERENCE TO RELATED APPLICATIONS

This application is a divisional of U.S. patent application Ser. No. 09/419,538, filed Oct. 18, 1999 now U.S. Pat. No. 6,254,614.

BACKGROUND OF THE INVENTION

For more than a century, it has been understood that breast cancers spread from the breast primarily by entering into and passing along lymphatic channels draining the breast. These channels pass into the armpit, into the skin and through the chest wall. Tumor spread is partly impeded by the presence of lymph nodes; in which tumor cells can remain and grow, or pass though and into the blood stream. Near the turn of the century, William Halsted proved the utility of this knowledge by surgically removing all possible lymphatic channels in addition to removing the breast. While this had the disadvantage of being a fairly mutilating procedure, he was able to reduce the rate of local recurrence of breast cancer to six percent from the previously reported recurrence rate of fifty to eighty-five percent when only the breast was removed.

Since the time of Halsted, surgical approaches have moved away from radical techniques toward tissue-sparing approaches. With the ability of earlier detection, minimal surgery; coupled with radiation and/or chemotherapy, has achieved similar results in preventing local recurrence. The problem of detection of tumor spread remains. Often, women who appear to have early stage disease will die of metastatic cancer despite a lack of evidence of spread. Therefore, breast cancer has been called a "systemic disease." This is most likely because cancer cells can spread undetected through lymphatic pathways; often early in the disease.

The primary determinant of survival in breast cancer is the presence or absence of tumor cells within the axillary (armpit) lymph nodes. Axillary nodes are removed to detect tumor spread and prevent recurrence. Tumor spread into other lymphatics that drain the breast is still undetectable, and probably accounts for cases of metastasis when the axillary lymph nodes are free of cancer. Lymphatic flow is determined by pressure and osmolar gradients. Increases in interstitial fluid or in externally applied pressure will enhance lymphatic flow. Entry of tumor cells into lymphatics is an active process of the tumor cells. Once in the lymphatic channels, tumor cells are carried along passively by the flow of lymphatic fluid. Any increase in interstitial fluid or pressure will, therefore, increase the rate of tumor spread.

Breast cancer can recur many years after initial treatment. Presumably, this is because of the undetectable spread of small numbers of tumor cells. While it has been known for many years that cutting into tumors can enhance their spread, present techniques of needle and core biopsies do just this. It has been claimed that these maneuvers don't spread cancer; however, the truth of these claims might not be apparent for many years.

Presently, the modalities of palpation, x-ray, ultrasound, and MRI are used to detect human breast cancers. Some of these techniques are used also for image-guided biopsy of breast tissue. Mammography is the mainstay of current early detection of breast cancer. This technique requires the forceful compression of the breast between plates to achieve acceptable images. Other known detection techniques, as previously mentioned, include ultrasound, magnetic resonance imaging (hereinafter "MRI"), and computerized tomography (hereinafter "CT"). Ultrasound images of the breast are obtained using a probe placed directly against the skin of the breast. MRI images are made by placing the breast in a magnetic field, between coils or hanging into a well that is surrounded by a coil. The principles of MRI are known to those of ordinary skill in the art. A description may be found in U.S. Pat. No. 5,437,280 to Hussman entitled "Magnetic Resonance Breast Localizer" which is hereby incorporated by reference in its entirety. Stereotactic biopsy techniques are done in a similar fashion; with a patient lying prone, with the breast hanging through a hole in the table. All these methods have shortcomings related to the flaccid nature of the breast which leads to difficulty in manipulating and orienting the organ. Additionally, some of these methods are very uncomfortable for the patient. The pain often associated with the forceful compression of the breast between plates in mammography being a prime example.

Early detection of breast cancers has spurred increasing interest in early intervention. Open biopsy techniques have given way to more image-guided biopsy methods which currently require forceful compression of the breast for stabilization, and require the forceful passage of instruments into the breast which often cause considerable bleeding; especially once the compression has been released. The tissue is in a distorted state and accurate removal of a specific volume of breast tissue is difficult. Present techniques for image-guided biopsy of the breast are limited by the size of the lesion to be removed, and by continuing challenges of bleeding and spread of tumor cells. Removal of lesions greater than a centimeter is generally not possible by these methods.

One object of the present invention is to allow for improved imaging and intervention in diagnosis and treatment of cancer, particularly early stage human breast cancer. Another object of the present invention is to allow for the accurate removal of tissue in a minimally bleeding or bloodless field.

SUMMARY OF THE INVENTION

One embodiment of the invention is a fixation apparatus for a breast comprising a cup-like body having a side wall with an open top end and an open bottom end and a fluid evacuation duct. The body defines a chamber adapted to receive a portion of the breast. A gasket is attached to the bottom end and is adapted to provide a substantially fluid tight seal between the body and an area of skin around the breast. A suction ring is attached to the top end and is adapted to provide a substantially fluid tight seal between the body and a second area on the breast. The apparatus may further include a hose attached to the fluid evacuation duct and connected to a pump capable of evacuating fluid in the cup-like body and mounted on the breast such that the gasket and suction ring provide a substantially fluid tight seal between the body and the first and second areas.

Another embodiment of the present invention is also a fixation apparatus for a protuberance of a body that comprises a cup-like body having a continuous wall and a port. The wall is open at one end and the wall defines a volume adapted to receive the protuberance without the protuberance contacting the wall. A gasket is attached to and adapted to provide a substantially fluid tight seal between the body and an area of skin around the protuberance. The fixation apparatus may further include a tubular member connecting the port to a pump for removing fluid to create a reduced or negative pressure within the volume and a pressure gauge connected to the fixation apparatus to monitor the pressure in the cup-like body.

Another embodiment of the present invention is a minimally invasive tissue saw. The tissue saw comprises a shaft extending along a first axis between a proximal end and a distal end and has a first cross section at the distal end. The tissue saw has a cutting head extending between a connecting end and a cutting end. The connecting end is pivotally connected to the distal end of the shaft so that at least a portion of the cutting head is able to swivel back and forth substantially along a second axis, the second axis in a direction transverse to the first axis. The cutting head has a cutting surface at the cutting end and extends across a width in the second axis and is able to swivel back and forth to cut a slit in tissue. The slit has a second cross section with the cutting head having at least one insertion surface substantially adjacent the cutting surface. The insertion surface extends between the connecting end and the cutting end and tapers from the first cross section at the connecting end to the second cross section at the cutting end. A portion of the insertion surface is a cauterizing element and extends around a strip of the insertion surface for cauterizing the tissue surrounding the slit.

In yet another embodiment the present invention is a minimally invasive device for removing a specimen of tissue with a cylinder extending along and rotatable around a first axis defined between a proximal end and a distal end. The cylinder has an interior surface and an exterior surface with a plurality of cutting arms. Each arm has an inner surface and an outer surface with the surfaces extending between a forward edge and a trailing edge. A portion of the forward edge defines a cutting edge and the cutting edge extends past the distal end of the cylinder to cut tissue. The arms are pivotally connected to the cylinder at the distal end and pivot between an open position and a closed position. The inner surface of each arm is adjacent to and substantially overlaps the exterior surface of the cylinder in the open position. A portion of the inner surface of each arm extends beyond the distal end of the cylinder and is adjacent tissue in the closed position.

Another embodiment of the invention is a minimally invasive tissue biopsy device comprising a cannula having a proximal end and a distal end and a first longitudinal axis defined between the ends. The device also includes a means for cutting a slit in tissue with the slit being in a second axis substantially transverse to the first longitudinal axis. The device further includes a trailing means for cauterizing substantially all of the tissue surrounding the slit.

Another embodiment of the invention is a method comprising: providing a retaining sleeve and a tissue saw. The retaining sleeve has a proximal and a distal end with the retaining sleeve having a first cross-section at the distal end. The tissue saw has an oscillating cutting head and a trailing coagulating element. The head has a cutting edge and a tapering insertion surface for advancing the retaining sleeve and the tissue saw along a first axis toward a lesion while the cutting edge oscillates back and forth and cuts an entry wound in tissue. The entry wound is a substantially linear slit having a second cross-section. The entry wound is distorted from the second cross-section of the slit to the first cross-section of the retaining sleeve. The tissue surrounding the slit is cauterized with the trailing coagulating element. The cauterization occurs as the tissue saw and retaining sleeve are advanced toward the lesion.

BRIEF DESCRIPTION OF THE DRAWINGS

FIG. 5 illustrates an embodiment of a tissue saw and retaining sleeve being introduced into an incision in the breast while held by a fixation apparatus of the present invention.

FIG. 6 illustrates a cross-section of the opening in the tissue cut by an embodiment of the tissue saw of the present invention.

FIG. 6A shows the transition between the cross-section of the opening cut into the tissue by a tissue saw of the present invention and the cross-section of the shaft or retaining sleeve which trails the cutting surface of the tissue saw.

DESCRIPTION OF THE PREFERRED EMBODIMENTS

Figure 1:
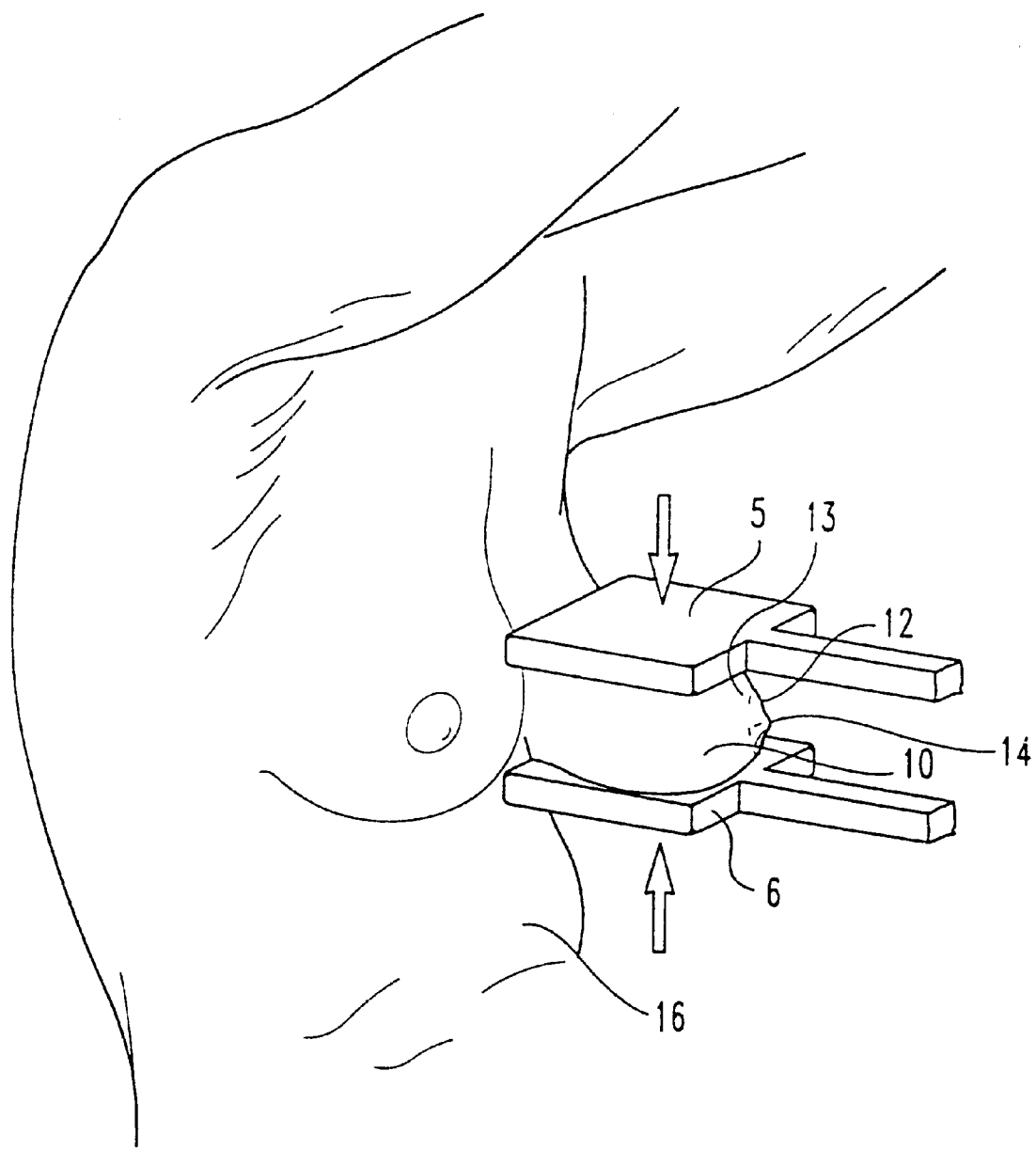
FIG. 1 illustrates the prior art form of breast fixation using compression plates.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such farther applications of the principles of the invention as illustrated therein being contemplated as would normally occur to one skilled in the art to which the invention relates.

All of the above-mentioned methods, such as mammography, ultrasound, MRI, etc., have shortcomings related to the flaccid nature of the breast which leads to difficulty in manipulating and orienting the organ. Additionally, some of these methods are very uncomfortable for the patient. One particular and well known discomfort is that associated with mammography as illustrated in FIG. 1. Breast 10 has a nipple 14 surrounded by an areola 12 which in turn is surrounded by periareolar skin 13. Breast 10 protrudes from chest wall 16 and is shown forcefully compressed between compression plates 5, 6 which is necessary to achieve acceptable images. This is in contrast to the situation found in various embodiments of the present invention.

Figure 2:
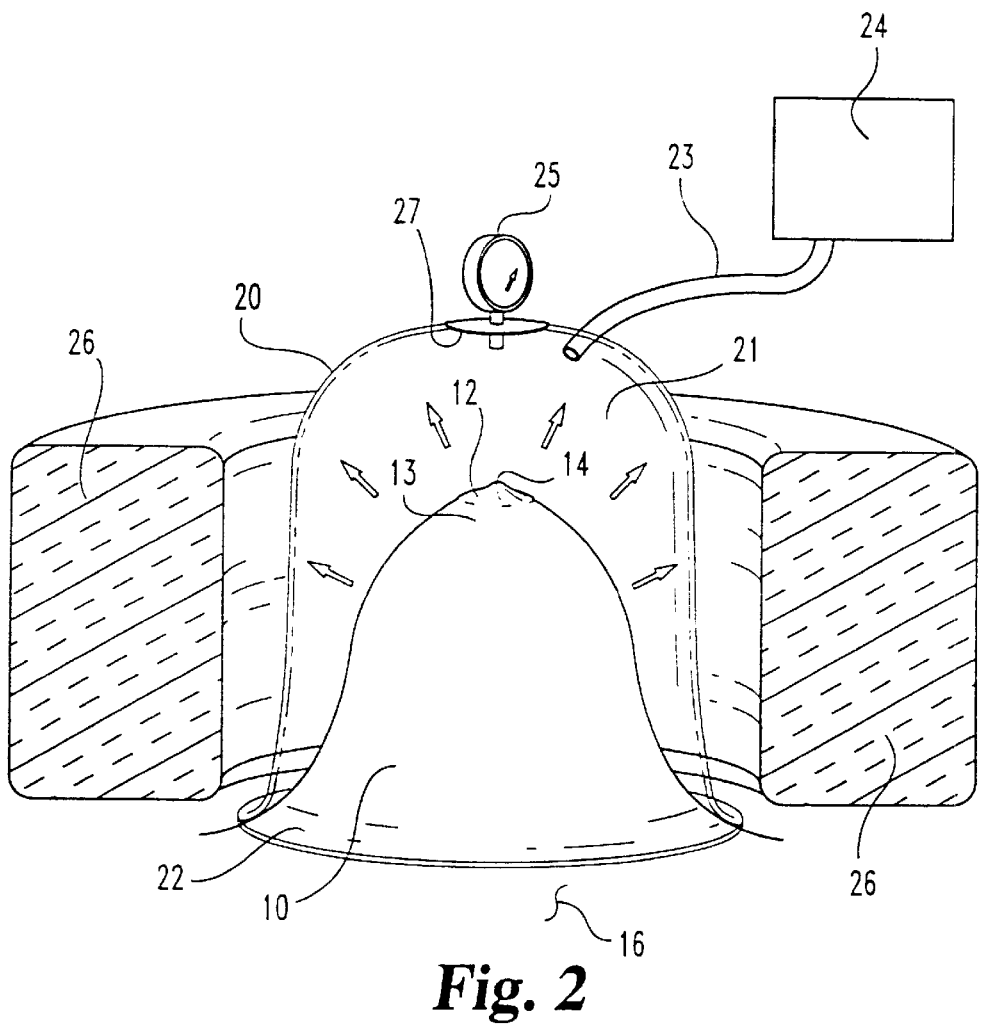
FIG. 2 is a side view partially in cross-section of an embodiment of the breast fixation apparatus of the present invention.

With reference to FIG. 2, an embodiment of the fixation device of the present invention in its simplest form is shown. The device comprises a cup-like body 20 defining a volume 21 containing the breast 10. It should be understood that the term cup-like body may include a variety of different shapes. These shapes include, but are not limited to, a frustospherical, frustoconical, generally hemispherical, funnel shaped, pyramidal, or even rectangular configurations which the cup-like body 20 may possess so long as it is capable of enclosing at least a portion of the breast 10. The breast 10 again has an areola 12 and nipple 14. The breast 10 is attached to the chest wall 16 as shown in FIG. 2. The cup-like body 20 is attached to the chest wall 16 by means of a flexible flanged gasket 22. It should be understood that if cup-like body 20 is appropriately shaped at its bottom end where gasket 22 is shown, the gasket 22 may instead be omitted and an adhesive applied directly to cup-like body 20 to attach it to the skin of the chest wall 16 or the breast 10. When such is the case, medical grade solvents may be applied at a later time to remove the apparatus.

The cup-like body 20, surrounding the breast 10, can be evacuated to varying degrees of negative pressure. While the flexible flanged gasket 22 is shown applied to the skin of the chest wall 16 around the breast 10, it is understood that the gasket 22 may also be attached directly to the skin of the breast 10 if so desired. The gasket 22 allows a fluid-tight seal to be formed in the cup-like body 20. Air or other fluids are removed from the volume 21 containing breast 10 by means of a vacuum pump 24 while a distending pressure is monitored by a pressure gauge 25. As the cup-like body 20 is evacuated, the breast 10 is drawn into the cup-like body 20 toward the top surface 27 and away from the chest wall 16.

Figure 3:
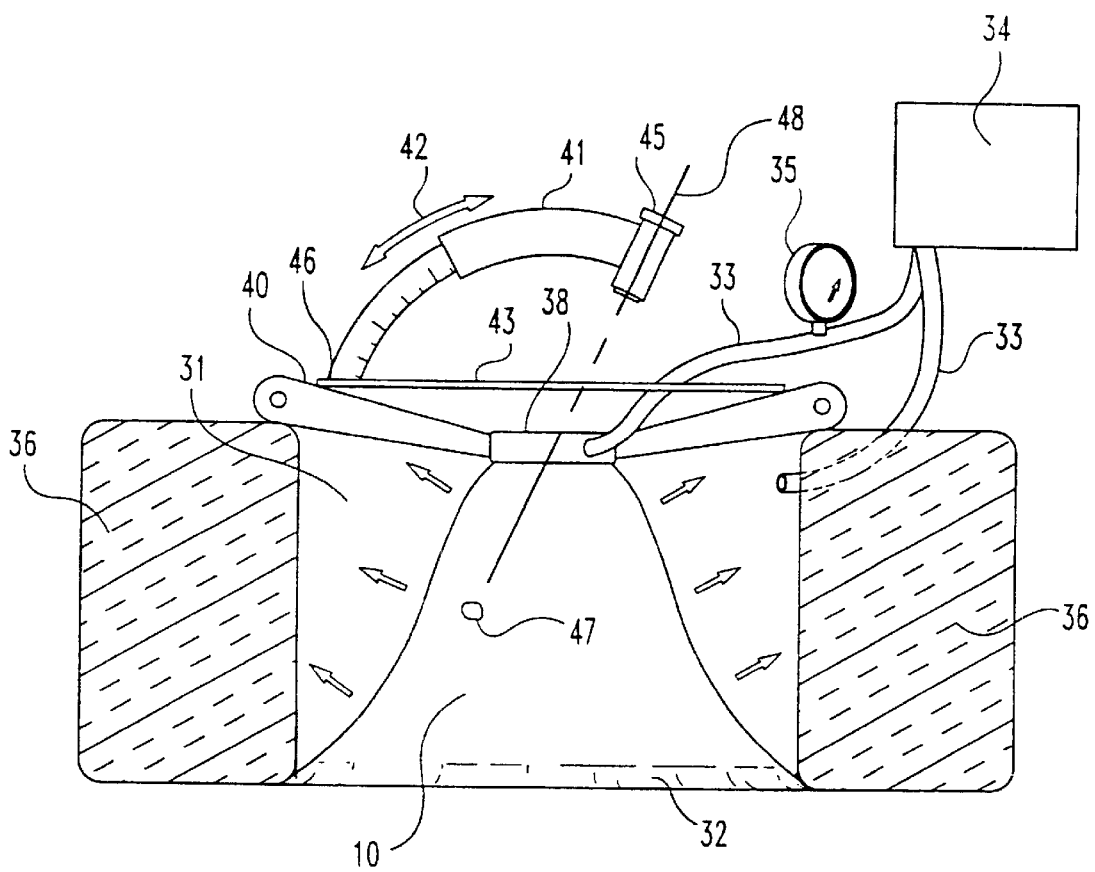
FIG. 3 is a partial sectional view of an alternative embodiment of the breast fixation apparatus of the present invention.

Since negative pressure is applied to all surfaces of the breast 10 evenly (as illustrated in FIGS. 2 and 3 with outwardly directed arrows), the breast 10 will expand to its maximum volume and remain in a fixed position away from the chest wall 16. In this position, the breast 10 can be placed in an imaging or interventional device 26. It should be understood that imaging or interventional device 26 may include, but is not limited to, devices such as an MRI coil, an ultrasound device, a CT scanner, or a radiation beam with any of these devices placed around or at a distance from the breast 10. Since fixation of the breast 10 is not dependent on gravity, the patient need not lay prone, but instead may be placed in many different positions for optimal advantage in imaging or irradiation as well as patient comfort.

Figure 4:
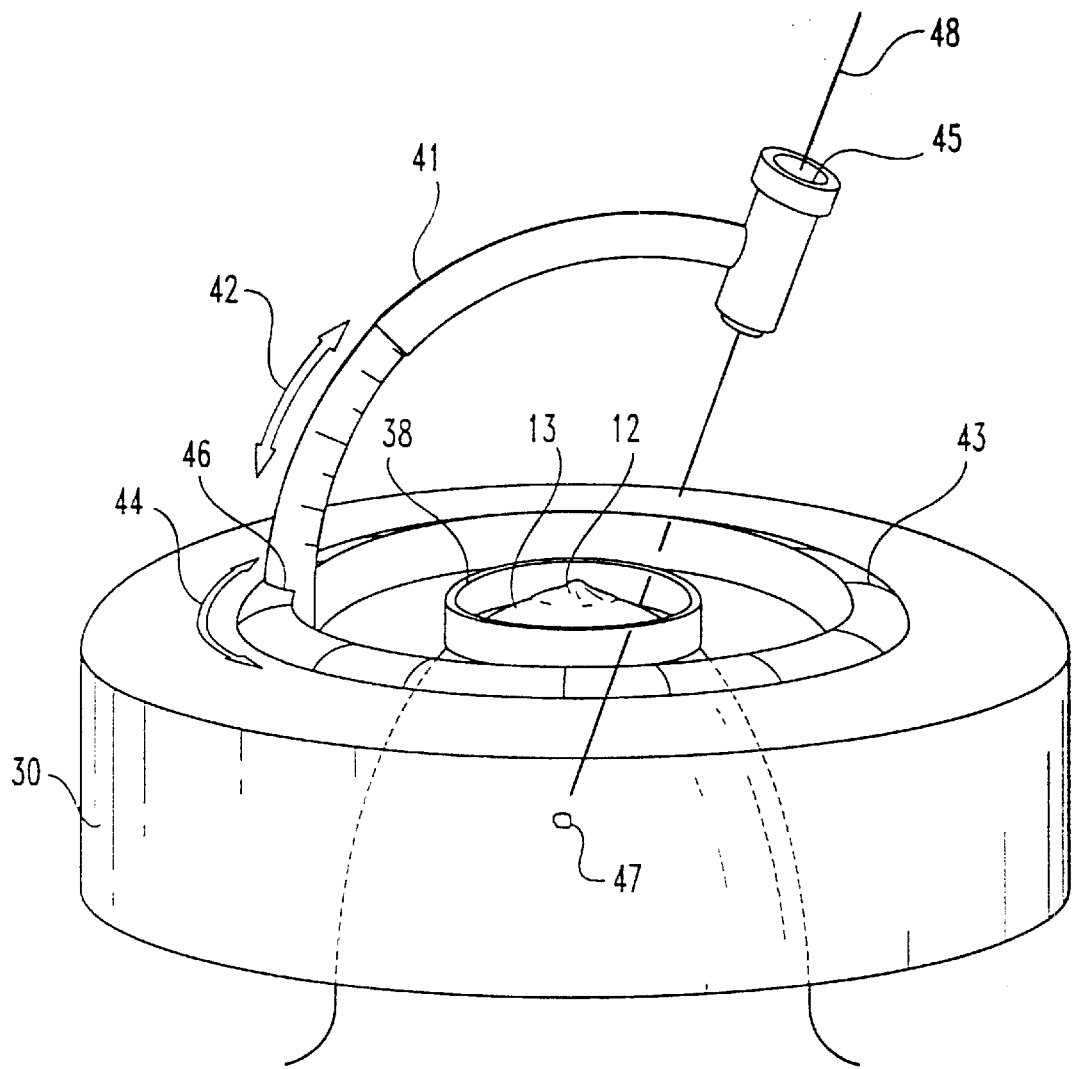
FIG. 4 is a enlarged perspective view of a portion of the embodiment of FIG. 3.
Figure 7A:
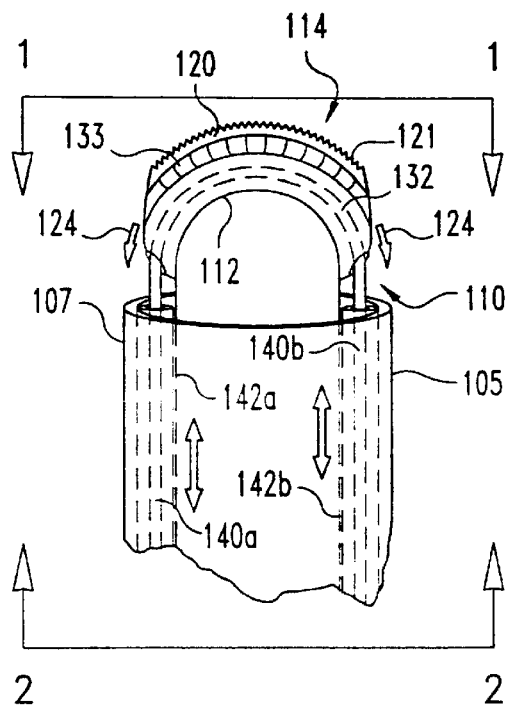
FIG. 7A is a top cross-sectional view of an embodiment of the tissue saw of the present invention.
Figure 7B:
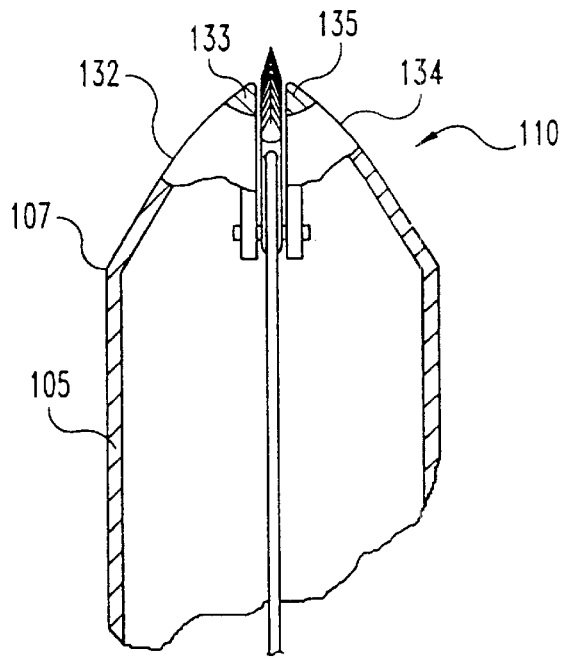
FIG. 7B is a side cross-sectional view of the embodiment of FIG. 7A.
Figure 8A:
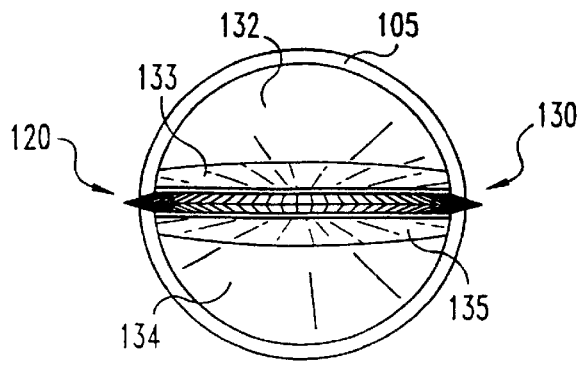
FIG. 8A is an end view of FIG. 7A along the lines 1—1.
Figure 8B:
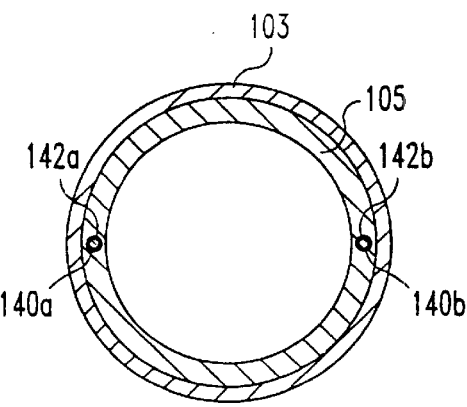
FIG. 8B is an end view of the embodiment of FIG. 7A along the lines 2—2.
Figure 9:
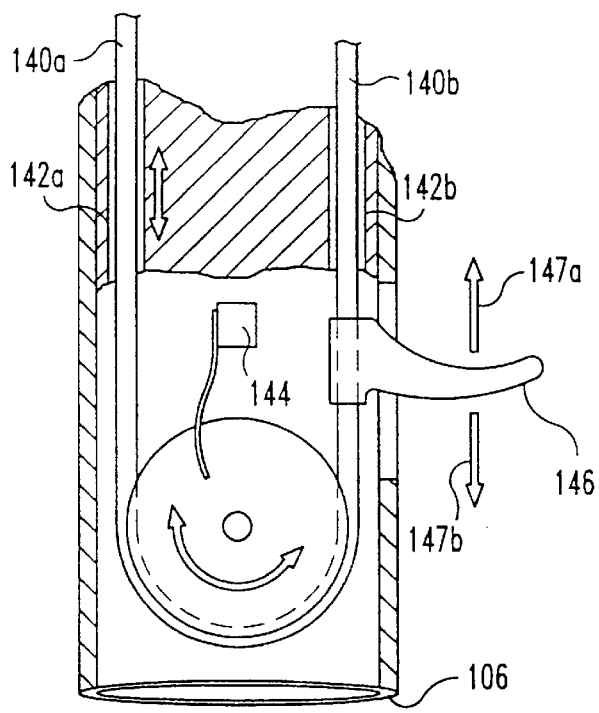
FIG. 9 is a top cross-sectional view of one example of a driving mechanism for the tissue saws of the present invention.

With references to FIGS. 3 and 4, another embodiment of the present invention is shown which facilitates image-guided intervention of the breast 10. In this embodiment, the cup-like body 30 again has a gasket 32 which together enclose a volume 31. As in the previous embodiment, cup-like body 30 may take a variety of configurations and shapes. The volume 31 enclosed includes at least a portion of the breast 10. As before, the cup-like body 30 may include one or more hoses 33 connected to a vacuum pump 34. In both embodiments, the cup-like body 20, 30 will have an evacuation duct or port of some kind to which the flexible tubular member or hose may be attached to allow for evacuation of air or other fluids from within the body 20, 30. It is again preferable to attach cup-like body 30 to the chest wall 16 by means of gasket 32 (with or without the use of an adhesive as desired).

In this preferred embodiment, however, the periareolar skin 13 is preferably left exposed. Thus, surgical intervention by a variety of instrumentation devices, one embodiment of which will be discussed further below, is possible through the periareolar skin 13. This is accomplished by providing a suction ring 38 which is applied to the periareolar skin 13 around the areola 12 of the breast 10. When the ring 38 is applied, it provides access to the periareolar skin 13 of the breast 10 outside the cup-like body 30, while maintaining negative pressure and fixation of the breast 10. Again, the distending pressure is preferably monitored by a pressure gauge 35. While suction ring 38 is shown applied to periareolar skin 13, it should be understood that a variety of sizes and locations for suction ring 38 are contemplated as within the scope of the invention. For example, suction ring 38 might be oval in configuration and not centered directly on the areola 12 thus exposing skin of breast 10 adjacent to the periareolar skin 13 if such is preferred for easier access during surgical intervention. Similarly, ring 38 might be larger in diameter and placed lower down on the breast 10 exposing more skin for easier access as required. It should also be understood that such variations in size and configuration are equally applicable to gasket 32. Thus, gasket 32 may be placed to create a substantially fluid tight seal between both the skin of the breast 10 as well as the skin of the chest wall 16 as desired.

The suction ring 38 is mounted on a adjustable stage 40 that can be adjusted for varying sizes of breast 10. The adjustable stage 40 acts as a platform for a variety of image-guided devices. It should be understood that a variety of other platforms are contemplated as within the scope of the invention that may contain alternative translational and/or rotational mechanisms for image-guided interventional devices. By way of small incisions, in or around the areola 12 and periareolar skin 13, various instruments and biopsy devices can be placed into the breast: guided by images from x-ray, ultrasound, MRI, or CT.

With reference to FIGS. 3 and 4, it is seen that one such adjustable stage 40 includes the ability for a 360 degree circumferential adjustment as indicated by the arrow 44 as well as an extensible holder which allows for adjustment in the azimuth direction as indicated by the arrow 42. In its simplest form, the adjustable stage 40 has a first portion 41 and a second portion 43. The first portion 41 may be extended or retracted for adjustment in the azimuth direction and terminates in a first end 45 in which a variety of image-guided devices may be attached. The second end 46 of first portion 41 is connected to the second portion 43 of adjustable stage 40. The second portion 43 of adjustable stage 40 is generally ring shaped and first portion 41 may be rotated about the circumference of second portion 43 and locked into position as desired. Similarly, the amount of extension of first portion 41 is also adjustable.

It is contemplated as within the scope of the invention that the suction chamber defined by cup like body 20, 30 can be of various sizes to accommodate equipment, coils, stages and the like. It should be understood that the chamber may detach from the imaging or interventional devices or both so that the breast could maintain a static position in space, as when being placed, first, in an imaging device and then into a targeting biopsy device. It should be further understood that the unique aspect of the present invention is the ability to stabilize the breast or other bodily protuberance in a position in space and that a wide variety of configurations of the chamber are contemplated as within the scope of the invention for achieving this end.

In one preferred embodiment the patient is lying prone and slightly tilted, bringing the breast into position with the suction chamber defined by the cup-like body. Then the imaging device may be arranged to be inside or outside the chamber, depending upon its particular requirements (e.g.— "surface coils" for MRI). As disclosed above, in one embodiment a secondary suction ring maintains exposure of the areola for entry using a variety of interventional devices, in particular biopsy devices. The secondary suction ring, being placed on an adjustable stage, aids in permitting a wide variety of configurations in arranging the chamber, imaging device, and interventional device as appropriate for particular surgical applications.

As shown in FIGS. 3 and 4, after the cup-like body 30 is evacuated, and the breast 10 fixed, imaging devices 36 may be used to locate precisely lesion 47 and then an interventional device shown as a line 48 in FIGS. 3 and 4 is inserted into the breast to precisely locate and excise the cancerous cells or tumor forming the lesion 47. A wide variety of interventional devices are contemplated for use in place of line 48 in FIGS. 3 and 4. Such devices may include, but are not limited to, those biopsy devices disclosed in U.S. Pat. Nos. 5,111,828, 5,197,484, and 5,353,804 all to Kornberg et al. as well as U.S. Pat. No. 5,795,308 to Russin and U.S. Pat. No. 5,817,034 to Milliman et al. all of which are hereby incorporated by reference. The preferred interventional devices, however, will be disclosed below as yet another embodiment of the present invention.

Thus, by way of small incisions, in or around the areola 12, various instruments and biopsy devices (guided by images from such things as x-ray, ultrasound, MRI, or CT) may be used to precisely treat the lesion 47 (or lesions) in the breast 10 which has been fixed in space. As is known by those of ordinary skill in the art, anatomically the breast is arranged radially in duct-lobule units spreading out from the nipple-areolar complex. (See pages 20–21 of *The Breast Cancer Survival Manual* by John Link, M.D., published by Henry Holt and Company, Inc., 1998, these pages are herein incorporated by reference). The fixation device of the present invention allows directed intervention along radial anatomic compartments, and consequently, allows more precise anatomic alignment for diagnostic and therapeutic intervention. It is seen that the various embodiments described above of the present invention may be used to fix the breast in a distended, stable position using negative pressure. The stable fixation of the breast in space is advantageous for breast imaging, tissue biopsy and specific local therapy.

Additional utility of the present invention derives from its ability to temporarily minimize or halt lymphatic flow from the breast and, thereby, halt the spread of tumor cells via the lymphatics. This is in contrast to present techniques which generally involve the forceful (and potentially painful) compression of the breast between two plates. This externally applied pressure enhances lymphatic flow (thus having the potential to increase the rate at which tumor cells spread) as opposed to minimizing or halting it. It is understood by those of ordinary skill in the art that cancerous cells are less dangerous if they remain intraductal. If a cancer becomes invasive or interductal, there is greater opportunity for the cancerous cells to spread. Every time a breast is compressed to the extent necessary to perform mammography, pressure in the system is increased. Increasing the pressure in the system increases the likelihood that the cancerous cells will either (1) be forced through the walls of the ductal tissue; and/or (2) increase the rate of lymphatic flow so that the cancer cells will filter through the labyrinth of the lymph nodes and the lymphatic system allowing the disease to spread to other portions of the body and progress to the systemic stage from localized. Thus, in addition to deriving utility from minimizing or halting lymphatic flow, the fixation device of the present invention is advantageous simply because it does not increase the pressure on the system, as is the case with many conventional techniques. The invention has further utility in applications such as those involving external beam radiation treatment. Both of the above disclosed embodiments for a breast fixator draw the breast 10 away from the chest wall 16 into a position more favorable to safe and specific treatment. It should be understood that the dimensions and materials of the above described embodiments can and will vary widely depending on the particular needs of the imaging or treatment modality. It should be further understood that the dimensions and materials of the device may also vary based on the size of the organ of the patient being treated.

Other advantages of the fixation device of the present invention are numerous. For example, a breast fixator provides the ability to stabilize the breast in space, both for imaging and for intervention. A fixation device as disclosed in the present application has particularly advantageous features for use with MR. With the breast fixed in space, different modalities can be applied and the patient can be moved from place to place. For example, MRI imaging takes some time, and keeping a patient in the scanner while doing a procedure wastes time for other imaging. However, by using a fixator to stabilize the breast as in the present invention, the breast can be imaged and the data/set of information about the breast can be stored and regenerated and manipulated. Once the data set is fixed, and the points on the fixator are referenced, the breast can be manipulated in a different place with different and cheaper localizing devices. In one preferred embodiment, the breast is fixed within a fixator which itself has coordinate markings. The breast is then imaged alone with the coordinating marks. The patient is then removed to an interventional area where, using ultrasound guidance within the superimposed data sets of ultrasound and MRI, the areas to undergo surgical intervention can be targeted. It is even possible to integrate MRI, ultrasound, and CT images of the breast and use all that information simultaneously. It should be understood that variations of the above described method of use of the breast fixation of the present application that would be known to those of ordinary skill in the art, are contemplated as within the scope of the invention. In particular, a variety of different imaging devices in connection with the interventional devices discussed above as well as the preferred embodiment discussed below are contemplated as within the scope of the invention.

With reference to FIGS. 5–18, there are illustrated various embodiments of a tissue saw and coring device for use in a minimally invasive procedure in a minimally bleeding or bloodless field and for removing a specimen of tissue. The specimen of tissue to be removed is that surrounding and including a lesion 80 found using the early detection methods of present technology. As previously indicated, the various embodiments of the tissue saw and coring devices disclosed below are intended to be used in conjunction with the breast fixation device of the present invention. It should be understood, however, that the devices and methods disclosed below may be used independently of the fixation device described above. It should be further understood that the tissue saw and coring devices discussed below will find utility with a wide variety of imaging devices including MRI. One preferred embodiment for use with MRI imaging modalities is if the tissue saw anchor the coring device, as well as any retaining sleeve used, are made of MR transparent materials. These MR transparent materials may include titanium, plastic (polycarbonate), and other materials known to those of ordinary skill in the art.

With respect to FIGS. 5–9, there is illustrated one embodiment of a minimally invasive tissue saw 101 for permitting access to a lesion 80 in a minimally bleeding or bloodless field. The tissue saw 101 is preferably first inserted through retaining sleeve 103. The retaining sleeve 103 may be held, for example, by the previously disclosed movable stage 40 (not shown) in the first portion 41 at the first end 45. The movable stage 40 (not shown) is aligned so that the tissue saw 101 lines up with an incision 90 in periareolar skin 13 and/or adjacent areola 12 and nipple 14. In its simplest form, the tissue saw 101 comprises a shaft 105 with an attached cutting head 110. The shaft 105 may be either a generally hollow cylinder or a solid rod (with passages as necessary for cables or other means for swiveling the cutting head 110) extending through the retaining sleeve 103. The retaining sleeve 103 is essentially a cylinder or cannula. A wide variety of shapes and forms other than the generally circular form shown for both the shaft 105 and retaining sleeve 103 are contemplated as within the scope of the invention.

Shaft 105 has a proximal end 106 and a distal end 107. Shaft 105 has a first cross-section 109 at distal end 107. The cutting head 110 has a connecting end 112 and a cutting end 114. The connecting end 112 of cutting head 110 is attached to the distal end 107 of shaft 105. As illustrated in FIGS. 5 and 6, the shaft 105 has a first cross-section 109 that is generally circular with a diameter 109a. The shaft 105 extends between the proximal end 106 and distal end 107 along a first longitudinal axis 108. The tissue saw 101 is intended to cut a slit 122. Slit 122 is cut by the cutting surface 120 of cutting head 110. Cutting surface 120 is shown with serrations 121. It should be understood that the use of serrations 121 at the cutting end of cutting surface 120, while preferred, is not necessary for operation of the present invention. Slit 122 is a long narrow aperture of minimal thickness having a width 125. Width 125 is defined in a plane of the second axis 116 which cutting head 110 creates by swiveling back and forth of cutting surface 120 in the direction of the arrows 124 (see FIGS. 5 and 7A).

While cutting surface 120 is illustrated as having serrations 121, it should be understood that alternative embodiments wherein the cutting surface is a generally smooth blade are contemplated as within the scope of the invention. In one embodiment, cutting surface 120 is an arc of a circle and has a width 125 (in the second axis 116 transverse to the first axis 108) equal to the diameter of either shaft 105 or retaining sleeve 103. It should be understood, however, that a variety of configurations and widths for cutting surface 120 are contemplated as within the scope of the invention. For example, cutting surface 120 may be an arc of a circle, a straight blade, polygonal, or some combination of the foregoing as known to those of ordinary skill in the art. It should be further understood that the cutting surface 120 may be a portion of the continuous perimeter of a generally circular bandsaw. This bandsaw may possess a wide variety of shapes and sizes. For example, the bandsaw may have a diameter at least equal to $\pi/2$ times the diameter of the shaft 105 or retaining sleeve 103 in which case no pivoting of the bandsaw would be necessary to cut a slit sufficiently large to encompass the retaining sleeve 103 or shaft 105. In an embodiment where the bandsaw had a diameter at least equal to $\pi/2$ times the diameter of shaft 105, the shaft 105 could be a generally hollow cylinder and the bandsaw could be detachable from the distal end 107 of the shaft 105, the bandsaw being collapsible so that it could be retracted through the shaft 105 and/or the retaining sleeve 103 as necessary. It is also contemplated as within the scope of the invention that a bandsaw might be used with a diameter equal to the diameter of the shaft 105 or retaining sleeve 103. In this embodiment, the bandsaw would need to pivot from side to side as discussed further below. The bandsaw could be rotated by various driving mechanisms known to those of ordinary skill in the art. One driving mechanism for a circular bandsaw would be an electric motor rotating in a continuous loop driving the circular bandsaw.

Cutting head 110 has an insertion surface 130 which provides a transition from the first cross-section 109 of shaft 105 to the second cross-section 123 of the slit 122. In the embodiments illustrated in the figures of the present application, insertion surface 130 is generally shown as comprising a first upper surface 132 having a first cauterizing plate or element 133 and a second lower surface 134 having a second cauterizing plate or element 135. It should be understood, however, that insertion surface 130 may be an integral whole extending around the entirety of the cutting head 110 and transitioning between first cross-section 109 and second cross-section 123. It should also be understood that instead of two surfaces 132 and 134, the insertion surface 130 may instead be made up of a plurality of surfaces as opposed to merely two. The transition between the first cross-sectional shape 109 of the shaft 105 and the second cross-sectional shape 123 of the substantially linear slit 122 may take a variety of configurations.

While upper surface 132 and lower surface 134 are shown as a straight line taper from the cutting surface 120 to the distal end 107 of shaft 105, it should be understood that a variety of profiles for the transition from the first cross section 109 of shaft 105 to the second cross section 123 of slit 122 are contemplated as within the scope of the invention. For example, upper surface 132 and lower surface 134 may be a series of steps, or a graduated transition that is concave or convex in shape or some combination of these and other configurations known to those of ordinary skill in the art. In either case, the upper surface 132 and lower surface 134 act to spread the tissue sliced by cutting surface 120 from the substantially linear slit 122 having second cross-sectional shape 123 into a shape corresponding to the first cross-sectional shape of shaft 105 or retaining sleeve 103.

The cutting head 110 is preferably pivotally connected to the distal end 107 of shaft 105. In one embodiment, the entire cutting head 110 will pivot. In other embodiments, however, only a portion of the cutting head 110 will be pivotally connected, such as the cutting surface 120. It should be understood that the term pivotally connected encompasses those situations in which cutting surface 120 slides along a track or other guide path located in between first upper surface 132 and second lower surface 134. In such an embodiment, the cutting surface 120 will pivot from side to side generally along the second axis 116. It should be understood by those of ordinary skill in the art that the width 125 of slit 122 is preferably, but not necessarily, at least a minimum distance to gain maximum benefit of the improvements of the present invention. Namely, basic geometric principles (see FIG. 6B) reveal that the circumference of the shaft 105 should be approximately equal to twice the width 125 of the slit 122. Thus, to introduce the retaining sleeve 103 up to the point of the lesion in a minimally bleeding or bloodless environment, a cutting surface 120 of cutting head 110 with a width 125 equal to the diameter of retaining sleeve 103 should have the ability to pivot to each side a distance of ($\pi/4-0.5$) times the diameter of the retaining sleeve 103 to be introduced into the body.

As previously mentioned, either the cutting head 110 in its entirety may swivel back and forth, or merely the cutting surface 120. In either situation, a variety of mechanisms are contemplated as within the scope of the invention for inducing the cutting surface 120 or cutting head 110 to swivel back and forth the necessary amount. For example, with reference to FIG. 7A and 8B, there is illustrated one driving mechanism for the swivel action of cutting head 110. In this embodiment, cables 140a and 140b running through cable shafts 142a and 142b are used to cause the necessary swiveling action. With respect to FIG. 9, there is shown a potential driving mechanism for the cables 140a and 140b running through cable shafts 142a and 142b. In this case, the driving mechanism utilizes a spring block 144 and a cutting trigger 146 intended to be moved back and forth along an axis as indicated by the arrows 147a and 147b.

It should be understood that an essential element of the tissue saw is the use of a cauterizing plate or element. The cauterizing plate or element may be placed on the cutting head 110, preferably, but not necessarily, adjacent the cutting surface 120. Thus, as the tissue saw 101 is advanced along the first axis 108, the tissue is first severed by the cutting surface 120 and then quickly cauterized by, for example, first cauterizing plate or element 133 and second cauterizing plate or element 135 so as to provide a minimally bleeding or bloodless field. This aids in preventing the spread of any tumor cells that might otherwise be released to flow elsewhere in the body by the cutting of the tissue, in particular the tissue surrounding or near a lesion 80. The cauterizing elements 133 and 135 both destroy any tumor cells encountered as well as causing coagulation in the tissue surrounding the slit 122.

The cauterizing elements 133, 135 may act to cauterize in a variety of manners including being an electrically resistive material so that they may act as an electric cauterizer, or as a conduit for fiber optic cables for laser coagulation and other mechanisms known to those of ordinary skill in the art. It should be understood that alternative locations for the cauterizing plate or elements are contemplated as within the scope of the invention. For example, while the cauterizing plate or elements 133, 135 may be located either adjacent cutting surface 120 or elsewhere on the cutting head 110, it should be understood that the strip of material acting as a cauterizing element may be placed in a variety of locations. For example, the cauterizing element could be a continuous strip of material placed around the circumference of the distal end 107 of shaft 105 or might even be placed around the circumference of a distal end of the retaining sleeve 103.

It should be further understood in some situations the shaft 105 will be a hollow cylinder and may also be acting as the retaining sleeve 103. In any case, the essential element of the tissue saw is that the cutting surface be followed by a trailing coagulating plate or strip of material which acts to cauterize the tissue surrounding the opening cut into the body by the cutting surface 120. It should also be understood that the first cauterizing element 133 and second cauterizing element 135 in the embodiment illustrated in the figures as well as discussed in the preceding text, may be either affixed to the insertion surface 130 or first surface 132 and second surface 134 (or the exterior of the shaft 105 or retaining sleeve 103 as may be the case) in a variety of manners known to those of ordinary skill in the art such as adhesives, welding, or being bolted on. Alternatively, it should also be understood that the cauterizing elements may be integrally formed upon whatever surface or surfaces are selected for their location.

Figure 10:
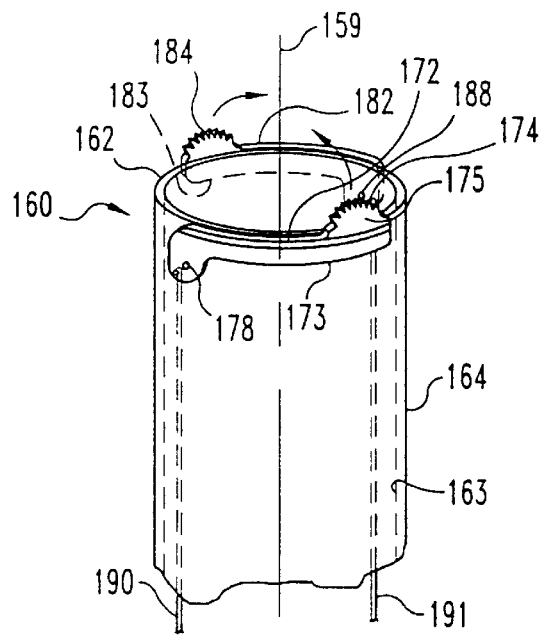
FIG. 10 is a perspective view of one embodiment of the coring device of the present invention.
Figure 12:
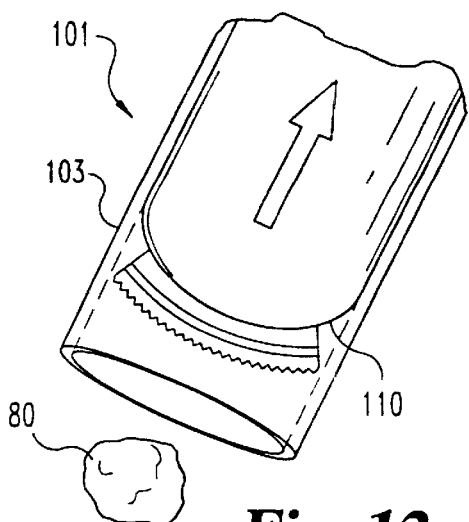
FIG. 12 is an illustration of the tissue saw being withdrawn through the retaining sleeve prior to encountering the lesion.
Figure 13:
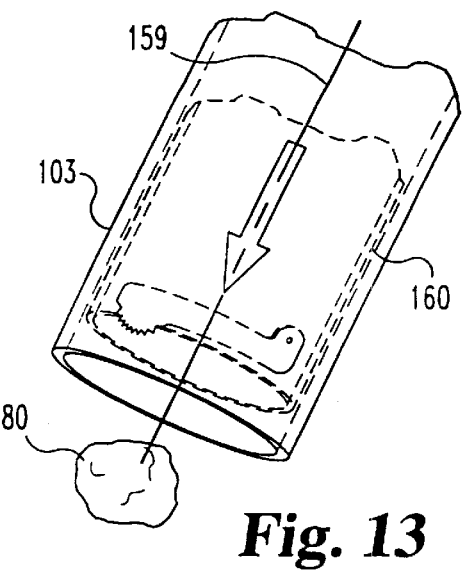
FIG. 13 is an illustration of the coring device of the present invention being advanced through the retaining sleeve toward the lesion.
Figure 14:
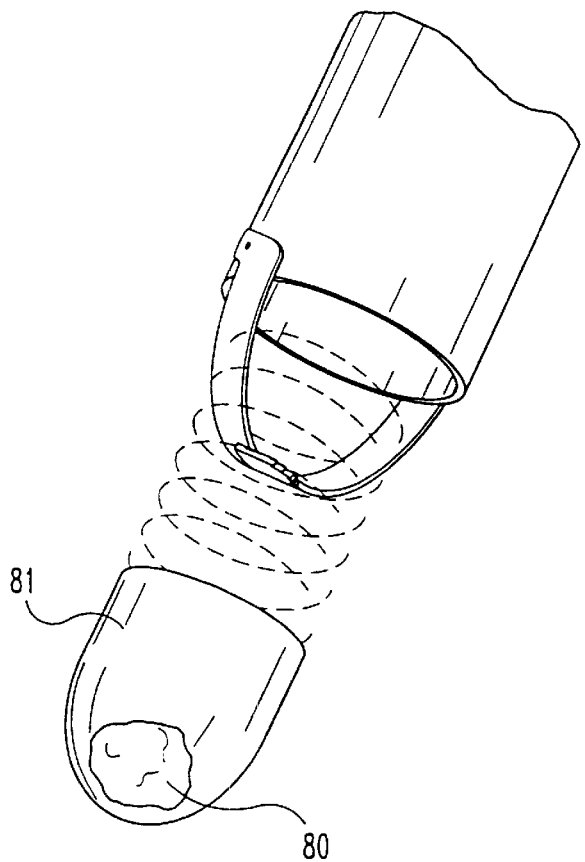
FIG. 14 illustrates the path the coring device of one embodiment of the present invention cuts into the tissue surrounding the lesion to be excised and the shape of the specimen of tissue cut.
Figure 15:
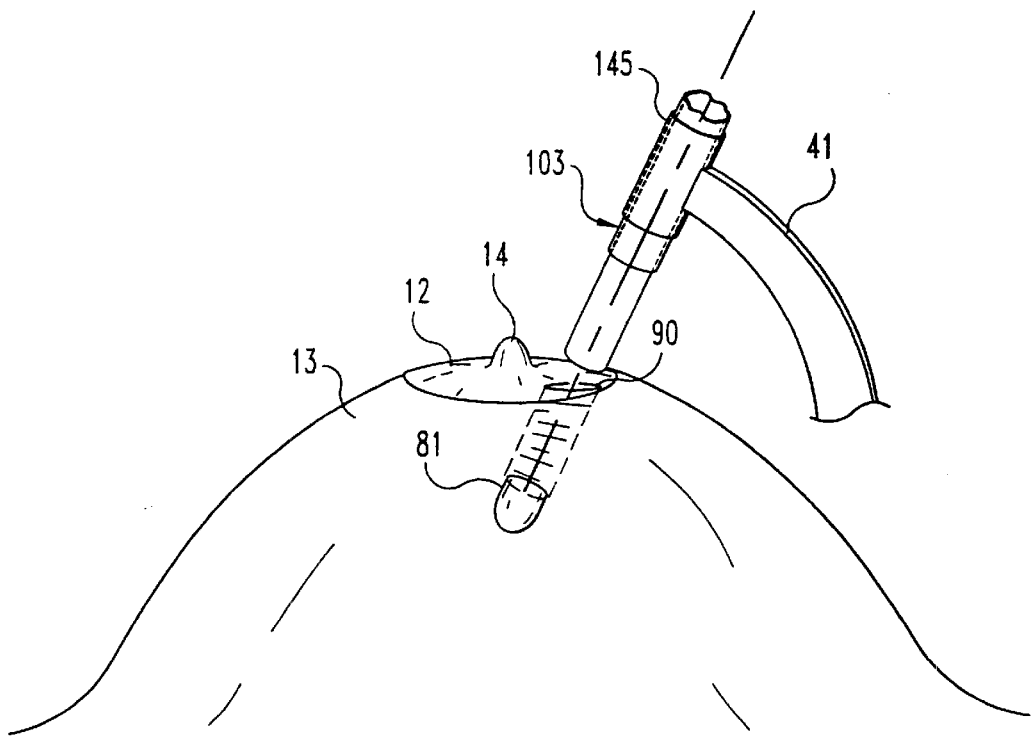
FIG. 15 illustrates the coagulated cavity and coagulated collapsing slit left behind after the withdrawal of the devices of the present invention.

With respect to FIGS. 10 and 11, one embodiment of the coring device for removing the specimen of tissue containing the suspected lesion 80 is illustrated. The device includes a cylinder 160 having a proximal end 161 and a distal end 162. The cylinder 160 extends generally along a first axis 159, the cylinder 160 rotating around the first axis 159, both to cut a circumference of a circle in tissue as well as rotating when cutting the bullet-shaped specimen 81 (see FIG. 14B) free as discussed below. Cylinder 160 has an interior surface 163 and an exterior surface 164. Cylinder 160 is preferably received within retaining sleeve 103 so that the exterior surface 164 of cylinder 160 is adjacent the interior surface 104a of the retaining sleeve 103.

It is understood that while it is preferred that the coring device be inserted up through the interior of the retaining sleeve 103, it is also possible to use a coring device with a cylinder 160 having a diameter 160a such that the cylinder 160 may be rotated around the exterior surface 104b of retaining sleeve 103. This is a less preferred embodiment, however, since the slit, (e.g., slit 122 with second cross-section 123) while having been distended by the insertion surfaces (such as first upper surface 132 and second lower surface 134) to the shape of the shaft 105 and/or the retaining sleeve 103, would require additional cutting and cauterizing to pass the cylinder 160 around the exterior 104b of retaining sleeve 103. In contrast, passing cylinder 160 through the interior of retaining sleeve 103 permits the introduction of the coring head 166 to the specimen of tissue 81 surrounding the suspected lesion 80 to be removed without further trauma.

Figure 11A:
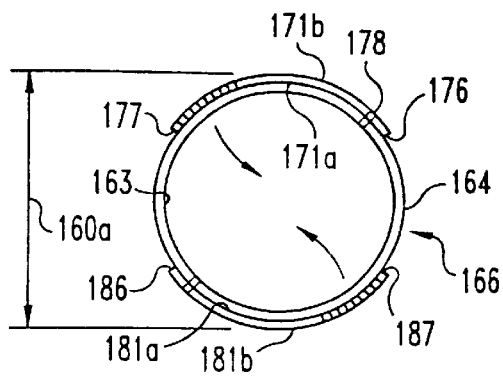
FIG. 11A is an end view of the coring device of FIG. 10 in the open position.
Figure 11B:
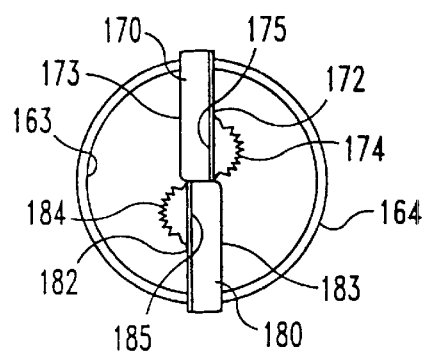
FIG. 11B is an end view of the coring device of FIG. 10 in the closed position.

With respect to FIGS. 10 and 11, there are illustrated various details of coring head 166. In the illustrated embodiment, coring head 166 is shown with first cutting arm 170 and second cutting arm 180. First cutting arm 170 has an inner surface 171a and an outer surface 171b extending between first forward edge 172 and first trailing edge 173. At least a portion of first forward edge 172 comprises a cutting edge 174 which may or may not be serrated as desired. Additionally, at least a portion of the first outer surface 171b of first cutting arm 170 acts as a first cauterizing element 175. The first cauterizing element 175 may be a coagulating plate or other means known to those of ordinary skill in the art for rapidly cauterizing the tissue cut by first cutting surface 174. First cutting arm 170 is generally swiveled around a first hinge 178 near first pivoting end 176. Distal from first pivoting end 176 is first far end 177. A first cable (or rod) 190 may be pulled so that first cutting arm 170 swivels from its open position (see FIG. 11A) to its closed position for a completed cut (see FIG. 11B).

In a similar manner, second cutting arm 180 has a second inner surface 181a and a second outer surface 181b extending between a second forward edge 182 and a second trailing edge 183. Second forward edge 182 has a second cutting edge 184 along at least a portion of second forward edge 182. It should be understood that second cutting edge 184, similar to first cutting edge 174, may or may not be serrated as desired. Also, second cutting arm 180 has a second cauterizing element 185 which, similar to first cauterizing element 175, may be attached or integrally formed with second outer surface 181*b*. As seen in FIGS. 10 and 11, second cutting arm 180 swivels from an open position to a closed position around a hinge 188 attached nearer to pivoting end 186 than to far end 187. Second cutting arm 180 is pivoted from its open position to its closed position using a second cable (or rod) 191 which is preferably attached near the pivoting end side of the second cutting arm and pulled, or which may instead be attached near the second far end 187 of second cutting arm 180 and pushed to force the second cutting arm 180 to swivel from its open position to its closed position. In the open position, second inner surface 181*a* is substantially adjacent the exterior surface 104*b* of retaining sleeve 103. In the closed position, the cutting edge 184 and cauterizing element 185 will have cut a bullet shaped specimen 81 (see FIGS. 14A–B) and cauterized the tissue surrounding the specimen 81 to be removed. It should be understood that first and second cauterizing elements 175, 185 are preferably, but not necessarily, found only on first and second outer surfaces 171*b*, 181*b*, respectively. Thus, the tissue specimen 81 being removed is preserved for microscopic analysis and further examination.

The cables 190, 191 will cause first and second arms 170, 180 to swivel across an approximately 90 degree arc from the open position to the closed position. A variety of mechanisms are contemplated as within the scope of the invention for causing the far ends 177, 187 of the first and second arms 170, 180 to curve inwardly toward one another and toward the first axis 159 about which the cylinder 160 rotates. One mechanism would be to manufacture the first and second arms 170, 180 out of a material having a memory. The memorized shape would be the inwardly curved shape of the closed position. As the first and second arms 170, 180 extended past the distal end of the cylinder 160, they would take on their memorized shape and the far ends 177, 187 would bend inwardly toward one another while rotating to cut free the dome shape at the end of the bullet-shaped specimen of tissue 81 to be removed. The arms may be made of a variety of materials such as stainless steel having a sufficient elastic strength, or even a shape memory material, such as nickel titanium alloy. Alternatively, a pair of springs (not shown) could be placed between the inner surfaces 171*a*, 181*a* of first and second cutting arms 170, 180 and the exterior surface 164 of cylinder 160. These springs would drive the pivoting ends 176, 186 away from the exterior surface 164 of cylinder 160 and would simultaneously cause the far ends 177, 187 to move inwardly toward the first axis 159 around which cylinder 160 rotates. It should be understood that a supporting armature which prevents the first and second cutting arms 170, 180 from returning to their memorized shape may be an apparatus attached to the cylinder 160 or the cylinder 160 itself may act as the supporting skeleton or framework.

The following is a description of the method of use of one embodiment of the above-described devices for use in permitting access to tissue surrounding a lesion in a minimally bleeding or bloodless field. The following also describes a method of use of one embodiment of devices in excising a specimen of tissue surrounding a lesion. Variations using other embodiments of devices disclosed above and below and other devices known to those of ordinary skill in the art are contemplated as within the scope of the invention.

For example, in one method of use, the second suction ring 38 is mounted on the movable stage 40 which has a targeting assembly (41, 42), which will adjust to 360 degrees and variable azimuth. Once the breast 10 is fixed in space, and the coordinates for the lesion 80 are determined, an incision 90 is made in or around the areola 12. Generally, incision 90 will be made by the surgeon using an ordinary scalpel or other cutting means known to those of skill in the art to preserve the skin's contour. Practicing surgeons will understand that the incision 90 and the scar it leaves behind are often the only visible measure a patient will have to use to judge the quality of the surgeon's work. Thus, it is preferable if incision 90 is made in a manner to preserve the skin's contour. It should be understood, however, that if desired, the tissue saw 101 may be used to create the incision 90 as well. After the incision 90 is made, the tissue saw 101 is advanced into the breast 10 toward the lesion 80. Around the tissue saw 101 is also advanced the retaining sleeve 103. It should be understood in some embodiments of the device the shaft 105 will be a hollow cylinder through which the cutting head 110 and other diagnostic and interventional devices may be extended through and retracted as necessary. In such cases, there may not be any need for a separate retaining sleeve 103.

It should also be understood that a wide variety of shapes and contours for the interior and exterior surfaces of the retaining sleeve 103 are contemplated as within the scope of the invention. For example, the retaining sleeve 103 may have an exterior surface 104*b* with a plurality of notches in it to act as a locking mechanism for more secure fixation to the targeting assembly (41, 42) and in particular whatever holding mechanism the first end 45 of the first portion 41 of movable stage 40 may have. Alternatively, it should be understood that the exterior surface 104*b* of retaining sleeve 103 may also be smooth and first end 45 may be a clamp permitting infinite variation in adjusting the position of retaining sleeve 103 with respect to the first end 45. A tissue saw 101 has an oscillating cutting head 110 with a leading cutting surface 120, which is preferably, but not necessarily provided with a plurality of serrations 121. The cutting head 110 has a trailing double coagulating plate (133, 135)—the tissue being first cut, and then exposed to cautery on both faces of the slit 122. Again, it is understood that the cauterizing element may be adjacent the cutting surface 120 or located some distance from it. Additionally, it should be further understood, that as previously discussed, the coagulating plate or other cauterizing element while preferably located on cutting head 110, may instead be located on shaft 105 or retaining sleeve 103.

As the tissue saw 101 is advanced, the substantially linear slit 122 will be enlarged to the cross-section 109 of shaft 105. The tissue saw 101 has a cutting edge 120 which is pivoted back and forth using a driving mechanism such as cables 140 run in the shaft 105. It should be understood that the cutting head 110's coagulation mechanism of first cauterizing plate 133 and second cauterizing plate 135 could be replaced with other mechanisms known to those of ordinary skill in the art such as a laser coagulating strip, or a series of fiber optic parts for trailing coagulation. The tissue saw 101 enables the placement of the retaining sleeve 103. The tissue saw 101 is then withdrawn (see FIG. 12) before the lesion 80 is encountered and the coring head 166 is preferably advanced (see FIG. 13) through the sleeve 103. It should be understood that retaining sleeve 103 permits introduction of other excisional devices and/or other diagnostic tools in a minimally bleeding or bloodless field.

In particular, it should also be understood that the coring head 166 could instead be advanced around the exterior surface 104b of retaining sleeve 103 as opposed to through the interior of the retaining sleeve 103. This is a less preferred embodiment, however, since the coring head 166 would then have to be rotated in its open position (see FIG. 11A) around the exterior surface 104b of the retaining sleeve 103 until it reached the distal end of the retaining sleeve 103. This would be less preferred to some extent since the coring head 166 would be inducing further trauma to the tissue as it was rotated and sliced through the tissue that was formerly adjacent the slit 122. However, such would not be unacceptable since coring head 166 also includes cauterizing elements or coagulating plates 175 and 185 on first cutting arm 170 and second cutting arm 180, respectively. Thus, the goal of a minimally bleeding or bloodless field would still be achieved. Additionally, the exterior surface 104b of the retaining sleeve 103 would in this embodiment act as an armature or supporting framework which would prevent the first cutting arm 170 and second cutting arm 180 from moving to their closed position until the extended past the distal end of retaining sleeve 103. This varies somewhat from the preferred embodiment in which a supporting skeleton or framework may be necessary at the distal end of the cylinder 160 around which the first cutting arm 170 and second cutting arm 180 are pivoted from their open position (see FIG. 11A) to their closed position (see FIG. 11B). It should also be understood that in some embodiments the cylinder itself will act as the armature supporting first cutting arm 170 and second cutting arm 180.

The remainder of the description of the method of use will be directed to the more preferred embodiment in which the coring head 166 is inserted through the retaining sleeve 103 as opposed to around the exterior surface 104b of retaining sleeve 103. It should be understood, however, that the less preferred embodiments and their variations are contemplated as within the scope of the invention and that the variations in the method of use between the below disclosure of the method of use for the most preferred embodiment and that for the less preferred embodiments will be readily apparent to those of ordinary skill in the art. At the end of the retaining sleeve 103, the coring head 166 will encounter the tissue and will begin to rotate. The two cutting arms 170, 180 will cut a cylinder of tissue using the cutting surfaces 174, 184, which preferably, but not necessarily include serrations, and as the first and second cutting arms 170, 180 are advanced and further rotated, the tissue will encounter the single external coagulating trailing plates 175, 185.

The 90 degree arc cutting arms 170, 180 are opposite each other across the diameter 160a of the coring head 166. As the coring head 166 is advanced beyond the lesion 80, the cutting arms 170, 180 are rotated beyond the end of the cylinder 160 as the cylinder 160 is no longer advanced. The arms will cut a "dome" (see FIG. 14A) beyond the end of the lesion plug 80 producing a bullet-shaped specimen 81 (see FIG. 14B). The entire device, along with the specimen 81, is withdrawn leaving a bullet-shaped coagulated cavity 82 and a coagulated collapsing slit 122 (see FIG. 15). It should be understood that the cutting arms 170, 180 may be rotated beyond the end of the cylinder by a variety of mechanisms. These mechanisms include such things as cables 190 and 191 attached near the pivoting ends of the respective cutting arms, or rods attached near the far ends of the respective arms to force them away from the distal end of the cylinder 160. Additionally, further forces directing the cutting arms from the open to the closed position may be generated by the use of springs placed in between the interior surface of the pivoting end of the cutting arms and the exterior surface of the cylinder 160.

Figure 16:
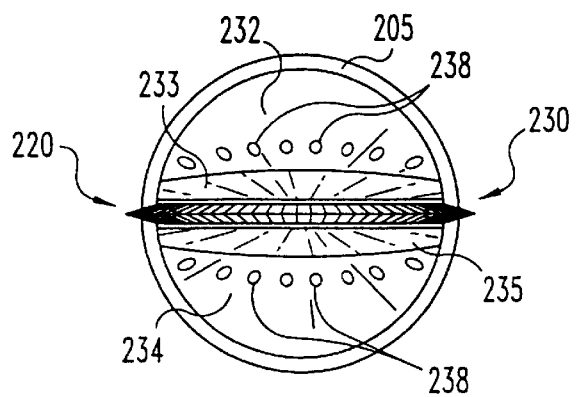
FIG. 16 is a top view of another embodiment of the tissue saw of the present invention.

With reference to FIG. 16, an alternative embodiment cutting head 210 is shown with like elements labeled as previously. Cutting head 210 has upper surface 232 and lower surface 234. In this embodiment, after the tissue encounters cauterizing elements 233, 235, it would then encounter a series of orifices 238 on the upper surface 232 and lower surface 234 of cutting head 210. These orifices 238 provide an injection port for the injection of anti-cancer agents, blood coagulation materials, and perhaps even polymeric substances to allow for the slow and somewhat controlled release of anti-cancer agents. The anti-cancer agents may include standard chemotherapeutic agents such as anti-metabolites which interrupt cell division. The anti-cancer agents may also be more specific surface receptors known to those of ordinary skill in the art such as tamoxifen or monoclonal antibodies. A description of one combination of blood coagulation agent, anti-cancer agent, and polymers is found in U.S. Pat. No. 4,536,387 to Sakamoto et al. which is hereby incorporated by reference. Due to the extreme toxicity of some anti-cancer agents, the application of the anti-cancer agents is thus made directly to the tissue surrounding the area of the lesion to be excised.

Figure 18A:
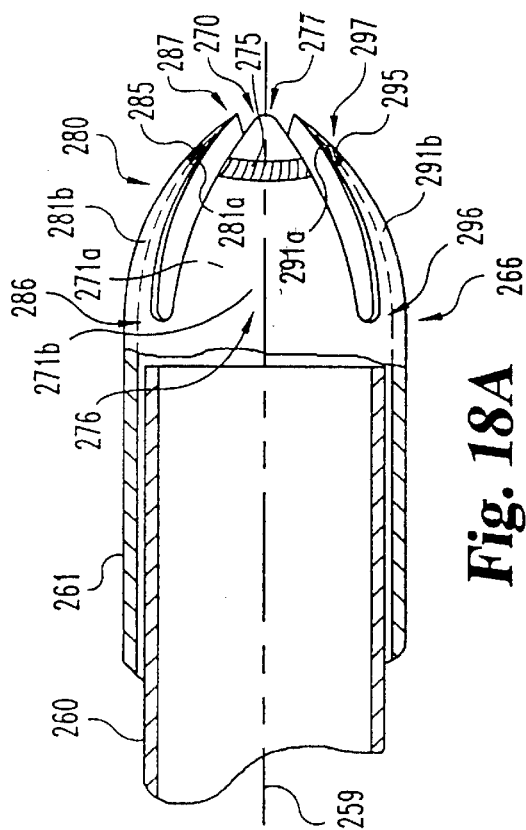
FIG. 18A is a side view of the coring device of FIG. 17A in the closed position.
Figure 18B:
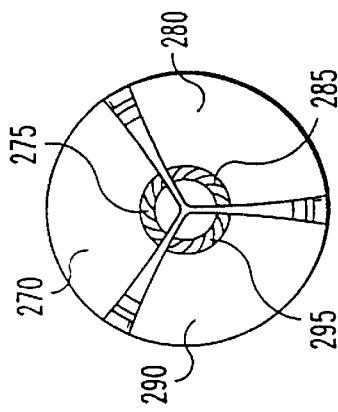
FIG. 18B is an end view of the embodiment of the coring device of FIG. 17A in the closed position.
Figure 17A:
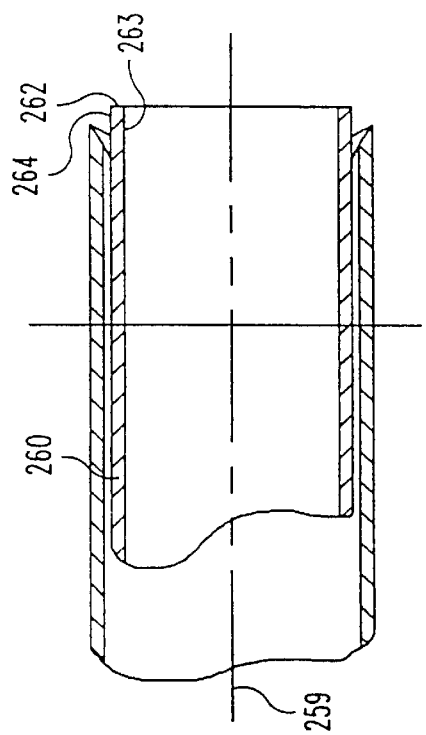
FIG. 17A is a side view of another embodiment of the coring device of the present invention.
Figure 17B:
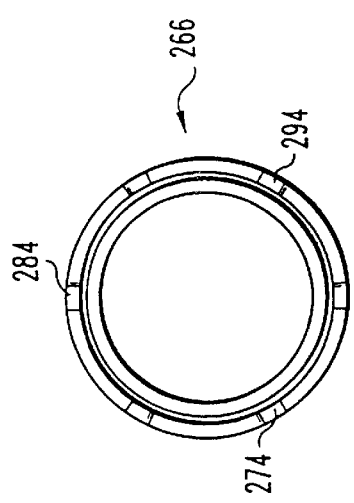
FIG. 17B is an end view of the embodiment of the coring device of FIG. 17A.

With reference to FIGS. 17 and 18 there is illustrated another embodiment of the coring device of the present invention. A coring device includes a barrel or cylinder 260 extending along a first axis 259 about which it rotates. The barrel 260 extends along first axis 259 between proximal end 261 (not shown) and distal end 262. The barrel 260 has an interior surface 263 and an exterior surface 264. At the distal end 262 of barrel 260 is the coring head 266. Coring head 266 includes first, second and third cutting arms 270, 280, 290 each having inner surfaces 271a, 281a, 291a and outer surfaces 271b, 281b, 291b extending between near ends 276, 286, 296 and far ends 277, 287, 297, respectively. The far ends 277, 287, 297 of each cutting arm 270, 280, 290 having cutting tips 274, 284, 294 for severing the tissue as barrel 260 is rotated around first axis 259 and advanced along the first axis 259 toward the targeted tissue. Trailing the cutting tips 274, 284, 294 on the outer surface 271b, 281b, 291b of the cutting arms 270, 280, 290 is a cauterizing element 275, 285, 295. Each of the cutting arms 270, 280, 290 has a supporting armature 272, 282, 292 (not shown) to hold the respective cutting arms in the open position. As the cutting tips 274, 284, 294 and the rest of the arm is extended past the respective armature, the arms 270, 280, 290 will go from the open position (see FIGS. 17A and 17B) to the closed position (see FIGS. 18A and 18B). It should be understood that the presence of armatures 272, 282, 292 extending from the distal end 262 of barrel 260 is just one of many variations contemplated as within the scope of the invention. As previously mentioned, the exterior surface 264 of barrel 260 may also act as a supporting skeleton or framework for the respective arms, thus obviating the need for any separate armature. It should be further understood that the wide variety of mechanisms previously discussed for inducing the cutting arms to curve inwardly are equally applicable in the present embodiment.

The above described embodiments of a biopsy device are intended for use with the previously described embodiments of a lymphostatic breast stabilizing device, which fixes the breast in space using negative pressure, and allows anatomical access to all parts of the breast using an image guided targeting device. The various embodiments of the biopsy device allow accurate removal of tissue cores from the breast; up to several centimeters in diameter; in a bloodless field. Other advantageous features include precise removal of cylindrical or bullet-shaped portions of the breast by a combination of cutting strategies using a unique tissue saw and coring device.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A medical apparatus comprising:
    a cylinder extending along and rotatable around a first axis defined between a proximal end and a distal end, the cylinder having an interior surface and an exterior surface;
    a plurality of cutting arms, each arm having an inner surface and an outer surface, the surfaces extending between a forward edge and a trailing edge, wherein at least a portion of the forward edge defines a cutting edge and wherein the cutting edge extends past the distal end of the cylinder to cut tissue;
    wherein the arms are pivotally connected to the cylinder substantially at its distal end, the arms pivoting between an open position and a closed position, the inner surface of each arm adjacent and substantially overlapping the exterior surface of the cylinder in the open position, and wherein at least a portion the inner surface of each arm extends beyond the distal end of the cylinder and is adjacent tissue in the closed position; and
    wherein each arm has a pivoting end and a far end, the forward edge and the trailing edge extending between the pivoting end and the far end, each of the arms pivoting substantially around the pivoting end.

2. The medical apparatus of claim 1, wherein at least a portion of the outer surface of each arm is a cauterizing element, the cauterizing element cauterizing the tissue surrounding a specimen of tissue to be removed.

3. The medical apparatus of claim 1, wherein the far end is adjacent and substantially overlapping the exterior surface of the cylinder in the open position, and wherein the far end has been pivoted 90 degrees in a direction away from the distal end of the cylinder in the closed position.

4. The medical apparatus of claim 1, wherein each of the arms is made of a material having a memory, the memory causing the arms to curve inwardly toward one another as the far end is pivoted from the open position to the closed position.

5. The medical apparatus of claim 4, wherein the arm is made of a shape memory material.

6. The medical apparatus of claim 1, further including a supporting armature attached to the cylinder, the arms curving inward toward one another as they move between the open position, wherein the arms substantially overlap the armature, to the closed position, wherein at least a portion of each arm no longer overlaps the armature.

7. The medical apparatus of claim 1, further including a spring located between the pivoting end of the inner surface of each of the arms and the exterior surface of the cylinder, the spring causing the far end of each arm to curve inwardly as the far end is pivoted from the open position to the closed position.

* * * * *